(12) United States Patent
Lu et al.

(10) Patent No.: US 8,921,075 B2
(45) Date of Patent: Dec. 30, 2014

(54) METHOD OF MANUFACTURING NANOPARTICLE CHAIN

(75) Inventors: Yen-Pei Lu, Hsinchu (TW); Ming-Yu Lin, Hsinchu (TW); Yu-Sheng Lai, Zhudong Township (TW); Yuh-Shyong Yang, Hsinchu (TW); Hsuen-Li Chen, Taipei (TW); Yu-Cheng Ou, Zhunan Township (TW)

(73) Assignee: National Applied Research Laboratories, Taipei (TW)

( * ) Notice: Subject to any disclaimer, the term of this patent is extended or adjusted under 35 U.S.C. 154(b) by 340 days.

(21) Appl. No.: 13/488,748

(22) Filed: Jun. 5, 2012

(65) Prior Publication Data
US 2013/0273610 A1    Oct. 17, 2013

(30) Foreign Application Priority Data

Apr. 12, 2012    (TW) .............................. 101113067 A

(51) Int. Cl.
*C12P 19/34*    (2006.01)
*C12Q 1/68*    (2006.01)

(52) U.S. Cl.
USPC ........................................ 435/91.2; 435/6.12

(58) Field of Classification Search
CPC ........... C12Q 1/6825; C12Q 2527/101; C12Q 2531/125; C12P 19/34; G01N 27/4145; A61F 2002/3084

USPC ................................................. 435/91.2, 6.12
See application file for complete search history.

(56) References Cited

PUBLICATIONS

Lin et al., Chem. Commun., Mar. 20, 2012, 48, 4902-4904.*
Zhao et al., Angew. Chem. Int. Ed., 2006, 45, 2409-2413.*
Beyer et al., NANO Letters, 2005, 5, 719-722.*
Li et al., Anal. Chem., 2010, 82, 2811-2816.*

* cited by examiner

*Primary Examiner* — Cynthia B Wilder
(74) *Attorney, Agent, or Firm* — Wang Law Firm, Inc.; Li K. Wang; Stephen Hsu

(57) ABSTRACT

A method of manufacturing a nanoparticle chain is disclosed. The method comprises the steps of: providing a single-stranded circular primer with a determined length, and amplifying the single-stranded circular primer into single-stranded DNA nanotemplate by an isothermal nucleotide amplification reaction such that an end of the single-stranded DNA nanotemplate is fixed to a surface of a substrate; and adding a single-stranded DNA probe conjugated with nanoparticle at one end of which, and attaching the single-stranded DNA probe to the corresponding sequence on the single-stranded DNA nanotemplate to form a nanoparticles chain. The method of manufacturing a nanoparticle chain further comprises providing a fluid, and the flowing direction of the fluid controls the aligning direction of the nanoparticle chain. Wherein, the inter-nanoparticle distance of the nanoparticle chain can be adjusted by adjusting a reaction temperature or adding the single-stranded DNA probe without conjugating with nanoparticles.

16 Claims, 8 Drawing Sheets ptern is transprinted thereon, and then an etching technique is used to remove the portion of extra material, so as to form the required shape. However, the nanostructure formed by this method cannot be adjusted further once the manufacturing process has been completed since the nanostructure is fixed on a surface. Obviously, such nanostructure has poor flexibility and stretchability. If it is necessary to fine tune the nanostructure, a new nanostructure must be formed on the surface again, and thus incurring higher manufacturing cost and longer manufacturing time.

METHOD OF MANUFACTURING NANOPARTICLE CHAIN

CROSS-REFERENCE TO RELATED APPLICATION

This application claims the benefit of Taiwan Patent Application No. 101113067, filed on Apr. 12, 2012, in the Taiwan Intellectual Property Office, the disclosure of which is incorporated herein in its entirety by reference.

BACKGROUND OF THE INVENTION

1. Field of the Invention

The present invention relates to a nanoparticle chain, and more particularly to a method of manufacturing a nanoparticle chain.

2. Description of Related Art

A nanoparticle is a small particle with a size falling within a range from 1 to 100 nanometers and some features of the nanoparticle are reduced size, weight and volume and an increased surface area, such that the physical and chemical properties including optical, magnetic, electrical and thermal properties of the nanoparticle varies according to its composite structure, shape, and particle size of the nanoparticle. Therefore, we can fine tune the physical and chemical properties such as the reflection and scattering of the nanoparticle by changing the structure or shape of the nanoparticle. Therefore, the nanoparticle is an advanced multifunctional material that plays an important role in the fields of chemistry, physics, biochemistry, medicine, and material science.

For example, a gold nugget has a golden metallic luster. However, if the inter-nanoparticle distance is greater than the average particle diameter, the solution containing dispersed gold nanoparticles is red in color. If the gold nanoparticles are clustered, the inter-nanoparticle distance will become smaller; and if the inter-nanoparticle distance is smaller than the average particle diameter, the solution will change its color from red to blue due to the absorbing effect of the surface plasmon resonance of the gold nanoparticles. Since the gold nanoparticle has obvious optical, chemical and catalytic properties, gold nanoparticles are used extensively in biochemical examinations. The surface plasmon resonance refers to a process of applying electromagnetic waves to gold nanoparticles in appropriate conditions, such that free electrons at the surface are excited to resulting in collective oscillation, and surface plasmon during this process is absorbed or scattered by the action of the electromagnetic waves at specific frequency and the surface plasmon. The oscillation of this sort is limited to the surface, so that the resonance condition is very sensitive to the shape of the surface and the surrounding environment. For example, the resonance frequency of the gold nanoparticles is related to the diameter of the particles.

The method of using a nanostructure of the nanoparticle to control the optical properties of the nanoparticles is a feasible solution. For example, the nanostructure can reduce reflection and scattering in the application of solar cells to improve the power generation efficiency of the solar cells. However, the feasibility of using a bottom-up method to assemble the nanoparticle structure is still questionable. For example, nano devices cannot be installed closely next to one another and disposed on the required structure, and the alignment of the nanostructure cannot be controlled precisely.

In a conventional method, a lithographical process must be used to form specific shaped nanostructure, and a mask formed on a surface of the nano material and a required DNA is the major chemical substance living organisms use to duplicate and store genetic information, and DNA has also been proven to be a very useful construction material on a nano scale. With the self-assembly nanostructure formed by DNA molecules, considerable potential exists for using nano material for the bottom-up nano manufacturing technology. The potential applications of the DNA self-assembly include nano electronics, biosensors and programmable/self-discipline molecular devices. Recently, DNA has been used for creating a periodical patterned structure, nano mechanical devices, and molecular computer systems. In addition, DNA with appropriate chemical substances is applied for guiding the assembly of other functional molecules. Therefore, DNA nanobiotechnology has become an emerging field of recent years.

In summation, the conventional nanoparticle structure still lacks flexibility and stretchability and has the drawbacks of a complicated manufacturing process and high manufacturing costs, and thus requiring improvements.

SUMMARY OF THE INVENTION

In view of the aforementioned problems of the conventional method of manufacturing nanoparticle structures that lacks of flexibility and stretchability and has the drawbacks of a complicated manufacturing process and high manufacturing cost, it is a primary objective of the present invention to provide a method of manufacturing a nanoparticle chain to overcome the aforementioned problems of the prior art.

To achieve the foregoing objective, the present invention provides a method of manufacturing a nanoparticle chain, comprising the steps of: providing a single-stranded circular DNA primer having a predetermined length, and amplifying the single-stranded circular DNA primer into at least one single-stranded DNA nanotemplate by an isothermal nucleotide amplification reaction, and fixing an end of the at least one single-stranded DNA nanotemplate to a surface of a substrate; and adding a plurality of single-stranded DNA probes, and an end of each single-stranded DNA probe being coupled to a nanoparticle, and attaching the single-stranded DNA probes to a corresponding sequence of the at least one single-stranded DNA nanotemplate to form at least one nanoparticle chain; such that the predetermined length of the single-stranded circular DNA primer is adjusted to control an inter-nanoparticle distance of the nanoparticle chain.

Preferably, the method further comprises the steps of: providing a fluid, and controlling the flowing direction of the fluid in order to control the aligning direction of the at least one nanoparticle chain after the step of adding the single-stranded DNA probes takes place.

Preferably, the at least one single-stranded DNA nanotemplate includes 18 to 3000 nucleotide bases.

Preferably, the single-stranded DNA probe includes 15 to 35 nucleotide bases.

Preferably the nanoparticle is a gold nanoparticle.

Preferably, the single-stranded circular DNA primer includes 60 to 120 nucleotide bases.

Preferably, when the predetermined length of the single-stranded circular DNA primer increases, the quantity of single-stranded DNA probes attached to the at least one single-stranded DNA nanotemplate decreases, and the inter-nanoparticle distance increases, so as to increase the inter-nanoparticle distance of the at least one nanoparticle chain.

In addition, the present invention further provides a method of manufacturing a nanoparticle chain, comprising the steps of: providing at least one single-stranded DNA nanotemplate, and an end of the at least one single-stranded DNA nanotemplate being fixed to a surface of a substrate, and the at least one single-stranded DNA nanotemplate having a secondary structure; adding a plurality of first single-stranded DNA probes, and an end of each of the first single-stranded DNA probes being combined with a nanoparticle and attached to a sequence corresponding to the at least one single-stranded DNA nanotemplate to form at least one nanoparticle chain having the secondary structure; adjusting a predetermined reaction temperature to change the secondary structure of the at least one nanoparticle chain; and adding a plurality of second single-stranded DNA probes attached to a sequence corresponding to the at least one single-stranded DNA nanotemplate; thereby, the predetermined reaction temperature is adjusted to control the secondary structure of the at least one single-stranded DNA nanotemplate in order to control the inter-nanoparticle distance.

Preferably, the method further comprises the steps of: providing a fluid, and controlling the flowing direction of the fluid in order to control the aligning direction of the at least one nanoparticle chain after the step of adding the first single-stranded DNA probes and the second single-stranded DNA probes takes place.

Preferably, the first single-stranded DNA probes and the second single-stranded DNA probes respectively include 15 to 35 nucleotide bases.

Preferably, the predetermined reaction temperature falls within a range from 25° C. to 70° C.

Preferably, when the predetermined reaction temperature increases, the secondary structure of the at least one nanoparticle chain is opened, so that the second single-stranded DNA probe is attached, and the at least one nanoparticle chain of the opened secondary structure cannot resume the secondary structure to increase the inter-nanoparticle distance, so as to adjust the inter-nanoparticle distance of the at least one nanoparticle chain.

In addition, the present invention further provides a method of manufacturing a nanoparticle chain, comprising the steps of: providing at least one single-stranded DNA nanotemplate, and an end of the at least one single-stranded DNA nanotemplate being fixed to a surface of a substrate; and adding a plurality of first single-stranded DNA probes and a plurality of second single-stranded DNA probes, and an end of each of the first single-stranded DNA probes being combined to a nanoparticle, and the second single-stranded DNA probes not combined with the nanoparticle, the first single-stranded DNA probes and the second single-stranded DNA probes competitively attached to a sequence corresponding to the at least one single-stranded DNA nanotemplate to form at least one nanoparticle chain; thereby, the first single-stranded DNA probes and the second single-stranded DNA probes have the same sequences, and the ratio of the first single-stranded DNA probes to the second single-stranded DNA probes is adjusted to control the quantity of the nanoparticles attached to the at least one single-stranded DNA nanotemplate, so as to control the distance between the nanoparticles.

Preferably, the method further comprises the steps of: providing a fluid, and controlling the flowing direction of the fluid in order to control the aligning direction of the at least one nanoparticle chain, after the step of adding the first single-stranded DNA probes and the second single-stranded DNA probes takes place.

Preferably, if the ratio of the first single-stranded DNA probes to the second single-stranded DNA probes increases, the quantity of the first single-stranded DNA probes competitively attached to the at least one single-stranded DNA nanotemplate increases, such that the inter-nanoparticle distance of the at least one nanoparticle chain decreases, so as to adjust the inter-nanoparticle distance of the at least one nanoparticle chain.

In summation, the method of manufacturing a nanoparticle chain of the present invention has one or more of the following advantages:

(1) The nanoparticle chain manufactured by the method of manufacturing a nanoparticle chain of the present invention features good flexibility, stretchability and directionality.

(2) The inter-nanoparticle distance of the nanoparticle chain manufactured by the method of manufacturing a nanoparticle chain of the present invention can be adjusted to change the light absorption wavelength of the nanoparticles.

(3) The aligning direction of the nanoparticle chain manufactured by the method of manufacturing a nanoparticle chain of the present invention can be adjusted to change the optical polarization of the nanoparticle chain.

(4) The inter-nanoparticle distance and the aligning direction of the nanoparticle chain manufactured by the method of manufacturing a nanoparticle chain of the present invention can be adjusted during an application to facilitate users' operations.

(5) Compared with the conventional lithographical process, the method of manufacturing a nanoparticle chain of the present invention features simple and easy operation procedures and low cost.

(6) The method of manufacturing a nanoparticle chain of the present invention requires no organic solvent, and thus complies with the requirements of environmental pollution.

DETAILED DESCRIPTION OF THE PREFERRED EMBODIMENTS

The technical contents and characteristics of the present invention will be apparent with the detailed description of a preferred embodiment accompanied with related drawings as follows. However, the preferred embodiment is provided for the purpose of illustrating the invention only, and not intended for limiting the scope of the invention.

Embodiment 1

Preparing a Nanoparticle Chain

The surface of a substrate is modified, and the DNA primer is fixed to the surface of the substrate.

Figure 1:
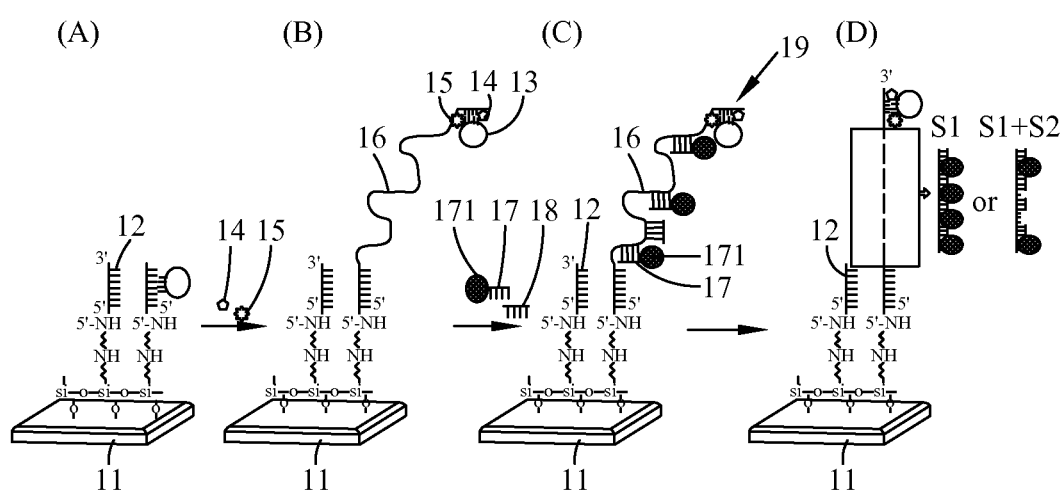
FIG. 1 is a schematic view of a method of manufacturing a nanoparticle chain in accordance with a preferred embodiment of the present invention.

With reference to FIG. 1 for a schematic view of a method of manufacturing a nanoparticle chain in accordance with an embodiment of the present invention, FIG. 1(A) shows that a self-assembly monolayer (SAM) is formed on the surface of the substrate 11 to serve as a covalent linker, and a DNA primer 12 is fixed to the surface of the substrate 11. In this embodiment, the self-assembly monolayer (SAM) can form the 3-aminopropyl triethoxysilane (APTES) on the surface of the substrate 11 by a silane reaction. At the self-assembly monolayer (SAM) formed on the surface of the substrate 11, the 5'-thiol-labeled DNA primer 12 is added and reacted at 4° C. overnight in order to fix the DNA primer 12 to the surface of the substrate 11. Wherein, the sequence and length of the DNA primer 12 can be designed freely according to requirements, and the DNA primer 12 of the present invention includes but is not limited to 18 nucleotide bases (approximately 6 nm).

Conjugated Single-Stranded DNA Probe and Nanoparticle

The nanoparticle is conjugated with the thiolated single-stranded DNA probe to hybridize the nanoparticle at a specific point of the single-stranded DNA nanotemplate. The nanoparticle is added into the 5'-thiol-labeled single-stranded DNA probes and reacted for 48 hours. After the nanoparticle/single-stranded DNA probe conjugate is centrifuged at 7000 to 10000 rpm, a supernatant is removed and then 100 µL of tris-HCl buffer (including 50 to 100 mM of tris-HCl and 10 to 30 mM of potassium chloride mixture) is added to complete the preparation of the nanoparticle/single-stranded DNA probe conjugate, and the conjugate is then stored at 4° C.

Forming a Single-Stranded DNA Nanotemplate

In FIG. 1(B), a nucleic acid amplification reaction mixture is added to the surface of the substrate 11 having the DNA primer 12 to perform an in situ isothermal nucleotide amplification reaction to form a nanoparticle chain. In this embodiment, a rolling cycle amplification reaction is used as an example for illustrating the isothermal nucleotide amplification reaction, but the invention is not limited to such arrangement only. In this embodiment, the nucleic acid amplification reaction mixture is a rolling cycle amplification mixture including a reaction buffer, phi29 DNA polymerase 14, T4 gene-32 protein 15, deoxyribonucleotide triphoshate (dNTP) and a single-stranded circular DNA primer.

More specifically, the rolling cycle amplification reaction includes the following steps: Adding a platelet-derived growth factor (PDGF) to induce the occurrence of a PDGF aptamer, and the PDGF aptamer can recognize the PDGF protein, and the PDGF aptamer is induced to deform and form a single-stranded circular DNA primer 13; and then adding phi29 DNA polymerase 14 and T4 gene-32 protein 15, to instigate a rolling cycle amplification reaction between the single-stranded circular DNA primer 13 and the DNA primer 12 fixed on the surface of the substrate 11, and the sequence of the single-stranded circular DNA primer 13 is amplified in the direction of 5' to 3' on the DNA primer 12 to form a single-stranded DNA nanotemplate 16. Wherein, phi29 DNA polymerase 14 promotes the DNA polymer to have a single-stranded DNA displacement (ssDNA displacement), and the T4 gene-32 protein 15 is a single-stranded DNA bonded protein, so that the single-stranded circular DNA primer 13 will not duplicate reciprocally.

Forming a Nanoparticle Chain

The aforementioned nanoparticle/single-stranded DNA probe conjugate is added to a substrate having a single-stranded DNA nanotemplate, such that the single-stranded DNA probe of the nanoparticle/single-stranded DNA probe conjugate is hybridized with the corresponding sequence of the single-stranded DNA nanotemplate to obtain a nanoparticle chain.

Figure 2:
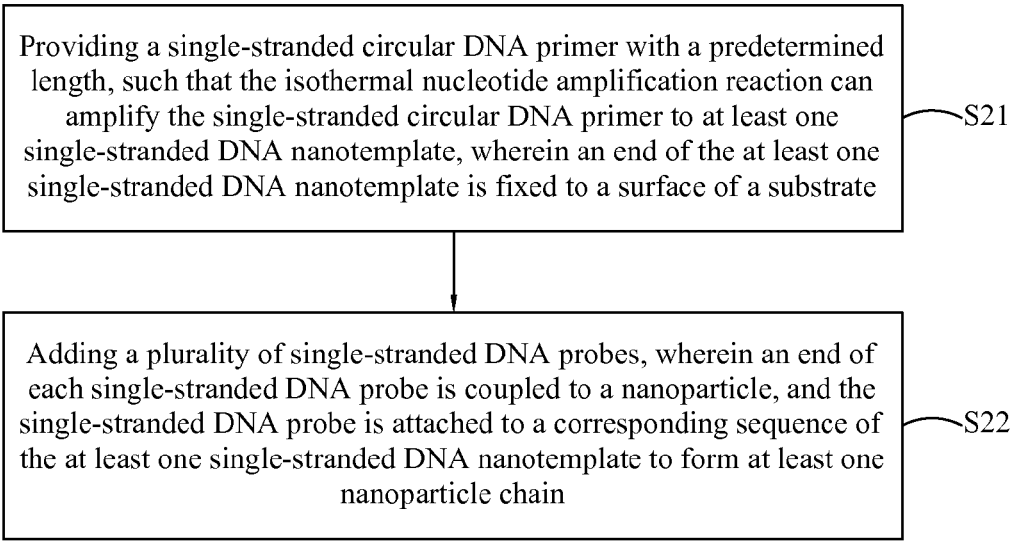
FIG. 2 is a flow chart of a method of manufacturing a nanoparticle chain in accordance with a preferred embodiment of the present invention.

Further, the method of manufacturing a nanoparticle chain of the present invention can change the length of the single-stranded circular DNA primer to change the length of the sequence of the single-stranded DNA nanotemplate repeatedly. With reference to FIG. 2 for a flow chart of a method of manufacturing a nanoparticle chain in accordance with an embodiment of the present invention, the method comprises the following steps. S21: Providing a single-stranded circular DNA primer with a predetermined length, such that the isothermal nucleotide amplification reaction can amplify the single-stranded circular DNA primer to at least one single-stranded DNA nanotemplate, wherein an end of the at least one single-stranded DNA nanotemplate is fixed to a surface of a substrate; and S22: Adding a plurality of single-stranded DNA probes, wherein an end of each single-stranded DNA probe is coupled to a nanoparticle, and the single-stranded DNA probe is attached to a corresponding sequence of the at least one single-stranded DNA nanotemplate to form at least one nanoparticle chain. Wherein, the sequence and length of the single-stranded circular DNA primer can be designed freely according to requirements. The single-stranded circular DNA primer of the present invention includes 20 to 120 nucleotide bases, and this embodiment includes but is not limited to 96 nucleotide bases (approximately equal to 33 nm).

In other words, when the predetermined length of single-stranded circular DNA primer increases, the inter-nanoparticle distance of the at least one nanoparticle chain increases. When the predetermined length of the circular primer decreases, the inter-nanoparticle distance of the at least one nanoparticle chain decreases.

Embodiment 2

Figure 3:
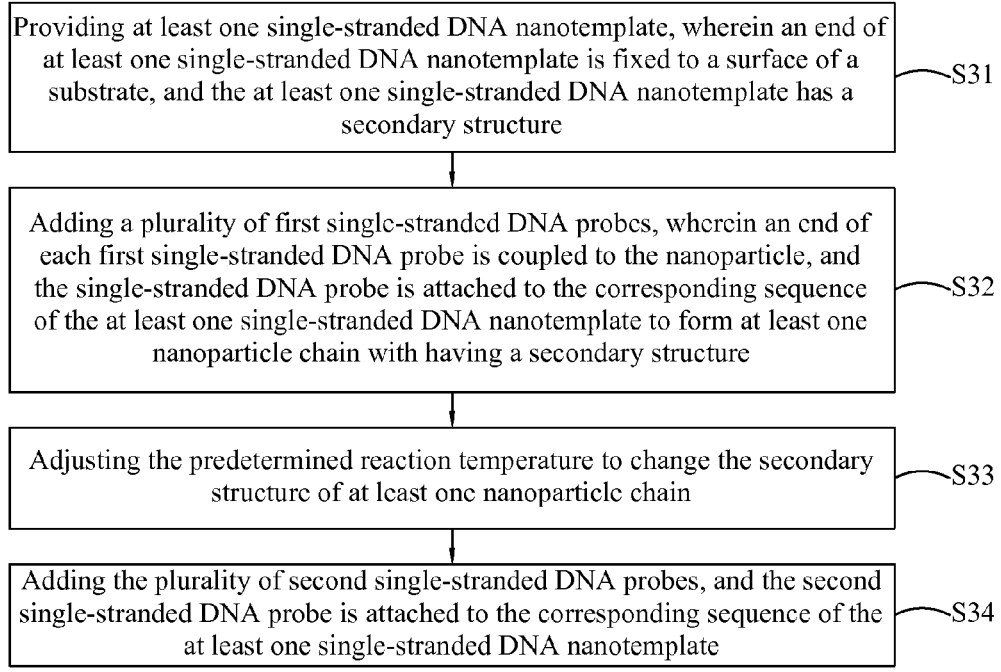
FIG. 3 is a flow chart of a method of manufacturing a nanoparticle chain in accordance with a preferred embodiment of the present invention.

The Reaction Temperature can be Adjusted to Change the Inter-Nanoparticle Distance of the Nanoparticle Chain With reference to FIG. 3 for the flow chart of a method of manufacturing a nanoparticle chain in accordance with an embodiment of the present invention, the method comprises the following steps: S31: Providing at least one single-stranded DNA nanotemplate, wherein an end of at least one single-stranded DNA nanotemplate is fixed to a surface of a substrate, and the at least one single-stranded DNA nanotemplate has a secondary structure; S32: Adding a plurality of first single-stranded DNA probes, wherein an end of each first single-stranded DNA probe is coupled to the nanoparticle, and the single-stranded DNA probe is attached to the corresponding sequence of the at least one single-stranded DNA nanotemplate to form at least one nanoparticle chain having a secondary structure; S33: Adjusting the predetermined reaction temperature to change the secondary structure of at least one nanoparticle chain; and S34: Adding the plurality of second single-stranded DNA probes, and the second single-stranded DNA probe is attached to the corresponding sequence of the at least one single-stranded DNA nanotemplate.

More specifically, the method of manufacturing a nanoparticle chain in accordance with this embodiment is substantially the same as the method of the foregoing embodiment, and the difference of this embodiment from the previous embodiment resides on that after the nanoparticle chain is formed, an UNAFOLD system is used to calculate a simulated secondary structure of the sequence of the nanoparticle chain, and estimate the change of quantity of the nucleotide base pairs stacked on the nanoparticle chain and free energy. After the nanoparticle chain is reacted with the sterilized deionized water at a specific temperature condition to open the secondary structure of the nanoparticle chain, and then the second single-stranded DNA probe is hybridized with the corresponding sequence of the uncombined first single-stranded DNA of the nanoparticle chain, and a microscope is used for the observation.

In other words, when the reaction temperature rises, the secondary structure of at least one single-stranded DNA nanotemplate is opened, such that the second single-stranded DNA probe is attached, and the at least one single-stranded DNA nanotemplate of the opened secondary structure cannot resume the secondary structure, so as to increase the inter-nanoparticle distance, and adjust the inter-nanoparticle distance of the at least one nanoparticle chain.

Preferred Embodiment 3

Single-Stranded DNA Probe Competition

Figure 4:
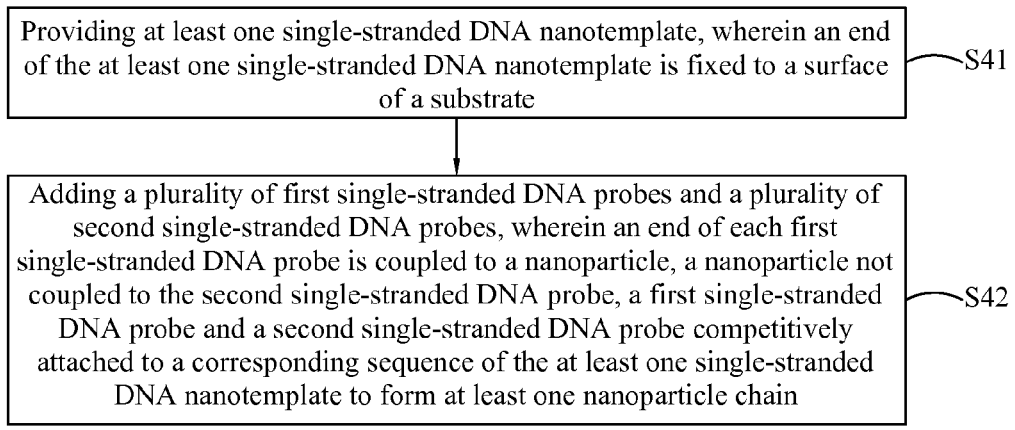
FIG. 4 is a flow chart of a method of manufacturing a nanoparticle chain in accordance with a preferred embodiment of the present invention.

With reference to FIGS. 1 and 4 for a schematic view and a flow chart of a method of manufacturing a nanoparticle chain in accordance with a preferred embodiment of the present invention respectively, the method as shown in FIG. 4 comprises the following steps. S41: Providing at least one single-stranded DNA nanotemplate, wherein an end of the at least one single-stranded DNA nanotemplate is fixed to a surface of a substrate; and S42: Adding a plurality of first single-stranded DNA probes and a plurality of second single-stranded DNA probes, wherein an end of each first single-stranded DNA probe is coupled to a nanoparticle, a nanoparticle not coupled to the second single-stranded DNA probe, a first single-stranded DNA probe and a second single-stranded DNA probe competitively attached to a corresponding sequence of the at least one single-stranded DNA nanotemplate to form at least one nanoparticle chain.

More specifically, FIGS. 1(C) and 1(D) show that the method of manufacturing a single-stranded DNA nanotemplate 16 in accordance with this embodiment is substantially the same as the method of the foregoing embodiment, and the difference of this embodiment from the previous embodiment resides on that the first single-stranded DNA probe 17 and the second single-stranded DNA probe 18 is added for the competitive reaction. Wherein, the first single-stranded DNA probe 17 and the second single-stranded DNA probe 18 have the same sequences, and an end of the first single-stranded DNA probe 17 is coupled to a nanoparticle 171, but an end of the second single-stranded DNA probe 18 is not coupled to a nanoparticle 171. If the percentage of the second single-stranded DNA probe 18 increases, then the inter-nanoparticle distance 171 of the at least one nanoparticle chain 19 will increase; and if the percentage of the second single-stranded DNA probe 18 decreases, then the inter-nanoparticle distance 171 of the at least one nanoparticle chain 19 will decrease.

Adjusting the Aligning Direction of the Nanoparticle Chain

In the experiment of processing the fluid, the deionized water flows through a surface of a substrate in a direction, but the deionized water is added to the middle of the substrate and let it sit still in a control, so that the control relates to no directionality.

Embodiment 4

Preferred Embodiment of the Present Invention

To allow persons ordinarily skilled in the art to implement the present invention, a preferred embodiment of the present invention is described below. It is noteworthy that all parameters and chemical agents used in the embodiment are provided for the purpose of illustrating the present invention only, and is not intended for limiting the scope of the invention.

Rolling Cycle Amplification (RCA) for Manufacturing Gold Nanoparticle Chain:

Prepare approximately $1 \times 10^{11}$ to $6 \times 10^{11}$ pieces of gold nanoparticles (with a particle diameter of 20 nm, provided by Sigma-Aldrich, USA). Add 220 to 280 pmoles of 5'-thiol-labeled single-stranded DNA probes for 48 hours of reaction to form a gold nanoparticle/single-stranded DNA probe conjugate. After centrifuging the gold nanoparticle/single-stranded DNA probe conjugate at 7000 to 9000 rpm, remove the supernatant. Adding 100 μL of tris-HCl buffer (containing 50 to 100 mM of tris-HCl, and 10 to 30 mM of potassium chloride mixture) to complete the manufacture of the gold nanoparticle/single-stranded DNA probe conjugate, and store the conjugate at 4° C. In this preferred embodiment, gold nanoparticles are used for example, but persons ordinarily skilled in the art should understand that other equivalent nanoparticles can be used instead.

On a surface of a substrate fixed with a DNA primer, add 50 μL of rolling cycle amplification reaction mixture (containing 40-70 mM of tris-HCl at pH 7.5, 50-90 mM of potassium chloride (KCl), 10-40 mM of magnesium chloride (MgCl2), 5-30 mM of ammonium sulfate ((NH4)2SO4), 0.88-3.5 mM of dNTP, 5-20 μg of T4 gene-32 protein, 10-30 units of Phi 29 DNA polymerase, and 0.23-2.8 nM of a single-stranded circular DNA primer) for reaction at room temperature for 2 hours.

In the rolling cycle amplification reaction mixture, the experiments are divided into four groups. In the first group, purely gold nanoparticles/single-stranded DNA probe conjugates (including the first single-stranded gold nanoparticle conjugated DNA probe, S1) are added. In the second group: 1-5 μL of the gold nanoparticle/single-stranded DNA probe conjugates and 1-3 μM of the second single-stranded gold-free nanoparticle conjugated DNA probe (S1+S2) mixed according to a ratio are added. In the third group, purely gold nanoparticles/single-stranded DNA probe conjugates are added and processed with a fluid (S1+w/Flow). In the fourth group, 1-5 μL of the gold nanoparticle/single-stranded DNA probe conjugate and 1-3 μM of the second single-stranded gold-free nanoparticle conjugated DNA probes mixed according to a ratio are added, and processed by a fluid (S1+S2+w/Flow), such that the gold nanoparticle/single-stranded DNA probe conjugate (S1) or the gold-free nanoparticle conjugated DNA probe (S2) on the substrate is specifically bounded with RCA's single-stranded DNA products to form a gold nanoparticle chain, and then deionized water is used to rinse the substrate thoroughly for three times, and then a microscope is used for observation and analysis. In the experiment of processing the fluid (w/Flow), the deionized water is allowed to flow across the surface of a substrate in a single direction, however in the control group, the deionized water is added to the middle of the substrate and letting it idle still, so that it does not have directionality.

Adjusting Reaction Temperature:

Use an UNAFOLD system to calculate a simulated secondary structure of a sequence of the nanoparticle chain with 384 nucleotides, and estimate the change of quantity of the nucleotide base pairs stacked on the nanoparticle chain and free energy. After the nanoparticle chain is reacted with the sterilized deionized water at 60° C. to open the secondary structure of the nanoparticle chain, add 1-5 µL of the second single-stranded DNA probe to hybridize with the nanoparticle chain, and use a microscope for observation.

Wherein, the reaction temperature of this embodiment is 60° C., but persons ordinarily skilled in the art should be able to analyze and adjust the reaction temperature according to the sequence of the nanoparticle chain. The reaction temperature generally falls within a range from 25° C. to 70° C., and preferably falls within a range from 37° C. to 60° C., but the invention is not limited to these temperatures only.

Experiment Results:

1) Forming Gold Nanoparticle Chain

Figure 5:
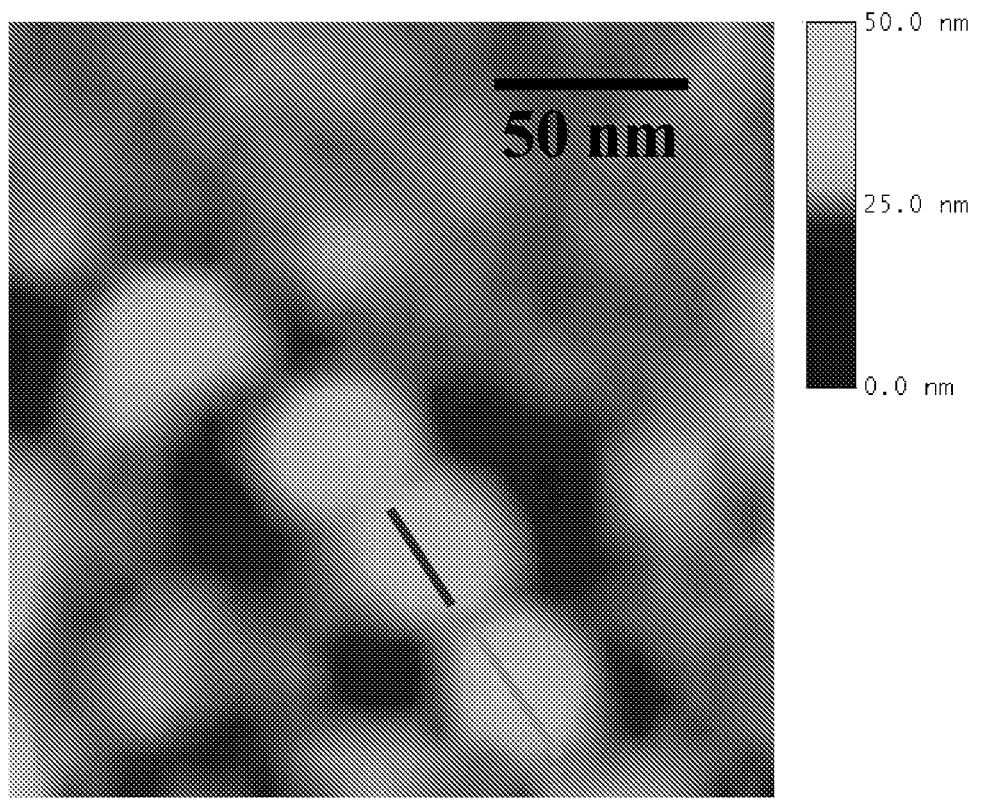
FIG. 5 is an atomic force microscope (AFM) diagram of a gold nanoparticle chain in accordance with a preferred embodiment of the present invention.
Figure 6:
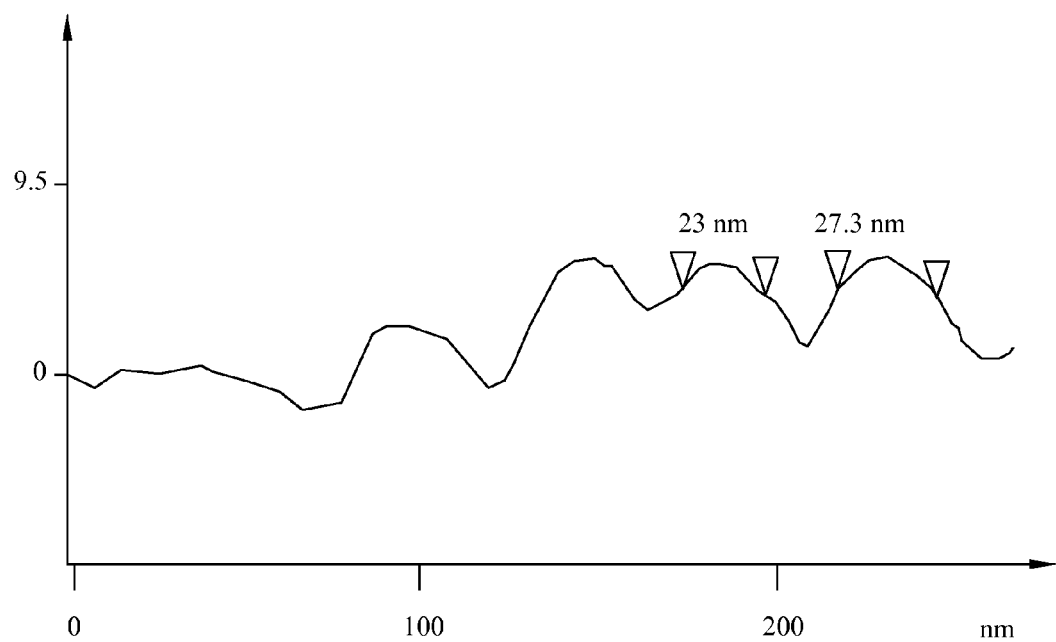
FIG. 6 is a schematic view of measuring the size of a gold nanoparticle in accordance with a preferred embodiment of the present invention.

With reference to FIGS. 5 and 6 for an atomic force microscope (AFM) diagram of a gold nanoparticle chain in accordance with a preferred embodiment of the present invention and a schematic view of measuring the size of the gold nanoparticle, the method arranges the gold nanoparticles into a chain, and the particle diameter of the gold nanoparticle is approximately 23 nm to 27 nm.

Figure 7:
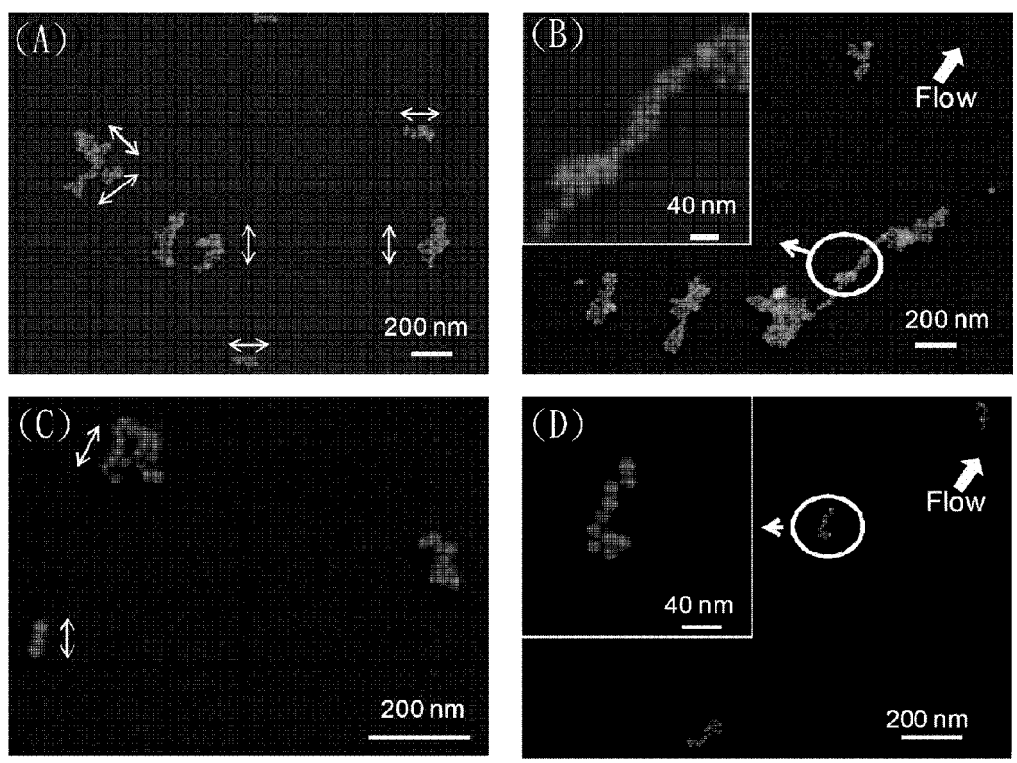
FIG. 7 is a scanning electron microscope (SEM) diagram of a gold nanoparticle chain in accordance with a preferred embodiment of the present invention.

2) Adding a Second Single-Stranded DNA to Increase the Inter-Nanoparticle Distance of a Gold Nanoparticle Chain With reference to FIGS. 7(A) to 7(D) for scanning electron microscope (SEM) diagrams of a gold nanoparticle chain in accordance with a preferred embodiment of the present invention, FIGS. 7(A) and 7(C) show the SEM diagrams of S1 and S1+S2 gold nanoparticle chains respectively. S1 and S1+S2 are used for evaluating the effect of adding the second single-stranded DNA probes not combined with the gold nanoparticle on the inter-nanoparticle distance of the gold nanoparticle chain.

In S1 and S1+S2, the same single-stranded circular DNA primer and the same reaction time are used for the reaction. The difference resides in that the S1+S2 further adds the second single-stranded DNA probe not combined with the gold nanoparticle into the first single-stranded DNA probe for competing the binding site of the single-stranded DNA nanotemplate. Theoretically, the inter-nanoparticle distance of the S1+S2 gold nanoparticle chain is greater than the inter-nanoparticle distance of the S1 gold nanoparticle chain. In the figures, the inter-nanoparticle distance of the S1 gold nanoparticle chain is significantly smaller than the inter-nanoparticle distance of the S1+S2 gold nanoparticle chain, probably because the second single-stranded DNA probe not combined with the gold nanoparticles wins the competition of the binding site over the first single-stranded DNA probe of the gold nanoparticles, so that less gold nanoparticles are combined with the single-stranded DNA nanotemplate, and the inter-nanoparticle distance of the gold nanoparticle chain becomes larger.

In other words, users can adjust the ratio of the single-stranded DNA probe combined with the gold nanoparticles to the single-stranded DNA probe not combined with the gold nanoparticles to adjust the inter-nanoparticle distance of the gold nanoparticle chain. The greater the ratio of the single-stranded DNA probe combined with the gold nanoparticles to the single-stranded DNA probe not combined with the gold nanoparticles, the smaller is the inter-nanoparticle distance of the gold nanoparticle chain. In other words, the relationship between the inter-nanoparticle distance and the particle diameter has a significant effect on the light absorbing wavelength, so that users can control the inter-nanoparticle distance to control the light absorbing wavelength of the nanoparticle chain while maintaining a constant particle diameter of the nanoparticles.

FIGS. 7(B) and 7(D) show the SEM diagrams of the S1+w/Flow and S1+S2+w/Flow gold nanoparticle chains respectively. Since the gold nanoparticle chain is bonded with a surface of a substrate by a covalent bond, so that after the deionized water is processed in the same direction, the gold nanoparticle chain is still fixed to the surface of the substrate and arranged along the direction of the flowing water. In other words, the users can adjust the water flow direction to control the alignment direction of the gold nanoparticle chain. When the aligning direction of the gold nanoparticle chain is controlled, the users can further control an optical polarization of the nanostructure composed of the gold nanoparticle chain.

Figure 8:
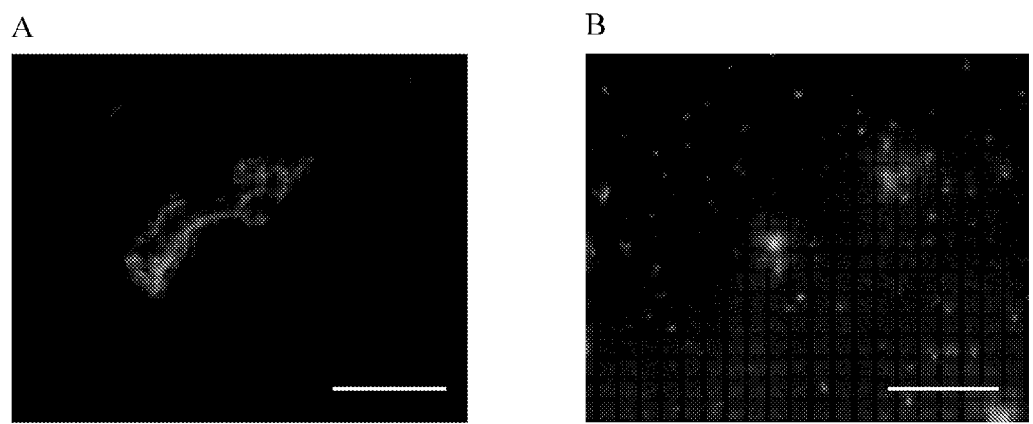
FIG. 8 is a dark field microscope (DFM) diagram of a heated gold nanoparticle chain in accordance with a preferred embodiment of the present invention.

3) Adjusting the Reaction Temperature to Increase the Inter-Nanoparticle Distance of a Gold Nanoparticle Chain With reference to FIGS. 8(A) and 8(B) for dark field microscope (DFM) diagrams of a heated gold nanoparticle chain in accordance with a preferred embodiment of the present invention, FIG. 8(B) shows that the reaction at the temperature of 60° C. can open the secondary structure of the single-stranded DNA nanotemplate effectively to increase the inter-nanoparticle distance of the gold nanoparticle chain. In other words, the users can change the reaction temperature to adjust the secondary structure of the single-stranded DNA nanotemplate, so as to change the inter-nanoparticle distance of the gold nanoparticle chain.

The method of manufacturing a nanoparticle chain of the present invention can manufacture a nanoparticle chain and control the inter-nanoparticle distance and the aligning direction of the nanoparticle chain, so as to control the light absorbing wavelength and the optical polarization of the nanoparticle chain. Therefore, the method of manufacturing a nanoparticle chain of the present invention can manufacture the nanoparticle chain by the bottom-up method and change the sequence of the single-stranded DNA nanotemplate by adjusting the reaction temperature, the biological competition or the single-direction fluid flowing method, so as to change the optical properties of the nanoparticle chain and complete a soft metal wire with diversified parameters.

In summation of the description above, the present invention breaks through the prior art and achieves the expected effects and complies with the patent application requirements, and is thus duly filed for patent application.

What is claimed is:

1. A method of manufacturing a nanoparticle chain, comprising the steps of:
   providing a single-stranded circular DNA primer having a predetermined length, and amplifying the single-stranded circular DNA primer into at least one single-stranded DNA nanotemplate by an isothermal nucleotide amplification reaction, and fixing an end of the at least one single-stranded DNA nanotemplate to a surface of a substrate; and
   adding a plurality of single-stranded DNA probes, and an end of each single-stranded DNA probe being coupled to a nanoparticle, and attaching the single-stranded DNA probes to a corresponding sequence of the at least one single-stranded DNA nanotemplate to form at least one nanoparticle chain;

wherein the predetermined length of the single-stranded circular DNA primer is adjusted to control an inter-nanoparticle distance of the nanoparticle chain.

2. The method of manufacturing a nanoparticle chain as recited in claim 1, further comprising the steps of providing a fluid, and controlling a flowing direction of the fluid in order to control an aligning direction of the at least one nanoparticle chain, after the step of adding the single-stranded DNA probes takes place.

3. The method of manufacturing a nanoparticle chain as recited in claim 1, wherein the at least one single-stranded DNA nanotemplate comprises 18 to 3000 nucleotide bases.

4. The method of manufacturing a nanoparticle chain as recited in claim 1, wherein the single-stranded DNA probe comprises 15 to 35 nucleotide bases.

5. The method of manufacturing a nanoparticle chain as recited in claim 1, wherein the nanoparticle is a gold nanoparticle.

6. The method of manufacturing a nanoparticle chain as recited in claim 1, wherein the single-stranded circular DNA primer comprises 60 to 120 nucleotide bases.

7. The method of manufacturing a nanoparticle chain as recited in claim 6, wherein when the predetermined length of the single-stranded circular DNA primer increases, a quantity of single-stranded DNA probes attached to the at least one single-stranded DNA nanotemplate decreases, and the inter-nanoparticle distance increases, so as to increase the inter-nanoparticle distance of the at least one nanoparticle chain.

8. A method of manufacturing a nanoparticle chain, comprising the steps of:

providing at least one single-stranded DNA nanotemplate, and an end of the at least one single-stranded DNA nanotemplate being fixed to a surface of a substrate, and the at least one single-stranded DNA nanotemplate having a secondary structure;

adding a plurality of first single-stranded DNA probes, and an end of each of the first single-stranded DNA probes being combined with a nanoparticle and attached to a sequence corresponding to the at least one single-stranded DNA nanotemplate to form at least one nanoparticle chain having the secondary structure;

adjusting a predetermined reaction temperature to change conformation of the secondary structure of the at least one nanoparticle chain; and adding a plurality of second single-stranded DNA probes attached to a corresponding sequence of the at least one single-stranded DNA nanotemplate;

wherein the predetermined reaction temperature is adjusted to control the secondary structure of the at least one single-stranded DNA nanotemplate in order to control an inter-nanoparticle distance of the nanoparticle chain.

9. The method of manufacturing a nanoparticle chain as recited in claim 8, further comprising the steps of providing a fluid and controlling a flowing direction of the fluid to control an aligning direction of the at least one nanoparticle chain, after the step of adding the second single-stranded DNA probes takes place.

10. The method of manufacturing a nanoparticle chain as recited in claim 8, wherein the predetermined reaction temperature falls within a range from 25° C. to 70° C.

11. The method of manufacturing a nanoparticle chain as recited in claim 10, wherein the secondary structure of the at least one nanoparticle chain is opened after the predetermined reaction temperature increases to attach the second single-stranded DNA probe, so that the at least one nanoparticle chain of the opened secondary structure cannot resume the secondary structure, to increase the inter-nanoparticle distance so as to adjust the distance between the nanoparticles of the at least one nanoparticle chain.

12. A method of manufacturing a nanoparticle chain, comprising the steps of:

providing at least one single-stranded DNA nanotemplate, and an end of the at least one single-stranded DNA nanotemplate being fixed to a surface of a substrate; and adding a plurality of first single-stranded DNA probes and a plurality of second single-stranded DNA probes, and an end of each of the first single-stranded DNA probes being combined to a nanoparticle, and the second single-stranded DNA probes not combined with the nanoparticle, the first single-stranded DNA probes and the second single-stranded DNA probes competitively attached to a corresponding sequence of the at least one single-stranded DNA nanotemplate to form at least one nanoparticle chain;

wherein the first single-stranded DNA probes and the second single-stranded DNA probes have the same sequences, and a ratio of the first single-stranded DNA probes to the second single-stranded DNA probes is adjusted to control a quantity of the nanoparticles attached to the at least one single-stranded DNA nanotemplate, so as to control an inter-nanoparticle distance of the nanoparticle chain.

13. The method of manufacturing a nanoparticle chain as recited in claim 12, further comprising the steps of providing a fluid, and controlling a flowing direction of the fluid in order to control an aligning direction of the at least one nanoparticle chain, after the step of adding the first single-stranded DNA probes and the second single-stranded DNA probes.

14. The method of manufacturing a nanoparticle chain as recited in claim 12, wherein the first single-stranded DNA probes and the second single-stranded DNA probes respectively comprise 15 to 35 nucleotide bases.

15. The method of manufacturing a nanoparticle chain as recited in claim 12, wherein the nanoparticle is a gold nanoparticle.

16. The method of manufacturing a nanoparticle chain as recited in claim 12, wherein if the ratio of the first single-stranded DNA probes to the second single-stranded DNA probes increases, a quantity of the first single-stranded DNA probes competitively attached to the at least one single-stranded DNA nanotemplate increases, such that the inter-nanoparticle distance of the at least one nanoparticle chain decreases, so as to adjust the inter-nanoparticle distance of the at least one nanoparticle chain.

* * * * *